United States Patent [19]

Déom et al.

[11] 4,196,631
[45] Apr. 8, 1980

[54] ULTRASONIC PROBE FOR MEASURING LIQUIDS AT HIGH TEMPERATURE AND UNDER HIGH PRESSURE

[75] Inventors: Alain A. Déom, Paris; Jean-Claude J. Démarais, Verrieres le Buisson, both of France

[73] Assignee: Office National d'Etudes et de Recherches Aerospatialles, Chattilon, France

[21] Appl. No.: 9,857

[22] Filed: Feb. 6, 1979

[30] Foreign Application Priority Data

Feb. 16, 1978 [FR] France ............................ 78 04352

[51] Int. Cl.² ............................................. G01N 29/00
[52] U.S. Cl. ........................................ 73/644; 73/703; 310/338
[58] Field of Search ................ 73/703, 644; 310/338, 310/336

[56] References Cited

U.S. PATENT DOCUMENTS

| 2,894,317 | 7/1959 | Marks | 310/338 |
| 3,378,705 | 4/1968 | Bacon | 73/644 |
| 3,602,744 | 8/1971 | Hugll | 310/338 |

FOREIGN PATENT DOCUMENTS

529385  3/1977  U.S.S.R. .................................. 310/338

Primary Examiner—Donald O. Woodiel
Attorney, Agent, or Firm—Abraham A. Saffitz

[57] ABSTRACT

An ultrasonic probe for measuring liquids at high temperature and under high pressure. The ultrasonic probe comprises a leak-tight protective sleeve which has an end face closed by a thin metallic wall. The protective sleeve contained internal elements which are in particular a transducing piezoelectric plate and a damping cylinder. The piezoelectric element has one face which is in mechanical and electrical contact with the internal face of the thin sleeve wall and the other face which is supported on a damping cylinder. The thin sleeve wall of the sleeve end face is constituted by a metallic layer obtained by cathodic sputtering.

5 Claims, 3 Drawing Figures

ULTRASONIC PROBE FOR MEASURING LIQUIDS AT HIGH TEMPERATURE AND UNDER HIGH PRESSURE

CROSS REFERENCES TO RELATED APPLICATIONS

Applicants hereby make cross references to their French Patent Application PV 78,04352, filed Feb. 16, 1978 and claim priority thereunder following the provisions of 35 USC 119.

BACKGROUND OF THE INVENTION

1. FIELD OF THE INVENTION

The invention relates to an ultrasonic probe for measuring liquids at high temperature and under high pressure, and more particularly to ultrasonic probes designed to produce or to detect ultrasonic wave beams. Such ultrasonic probe are generally used for measuring speeds or flow rates of corrosive or noncorrosive liquids which circulate under pressure and at high temperature in piping.

2. DESCRIPTION OF THE PRIOR ART

Probes which may be used for measurements of the above type are known, but their use is limited to maximum temperatures of approximately +80° C. and maximum pressures of approximately 100 bars.

Such a probe generally comprises a leak-tight monobloc cylindrical body or sleeve one of whose ends is closed by a thin wall which constitutes the front transmitting or receiving face for the ultrasonic waves. The thin wall should be leak-tight, able to withstand pressure and temperature, chemically inert with respect to the medium in which the probe is to operate and must also enable propagation of the ultrasonic beam in both directions with adequate transparency and good directional characteristics.

The French Pat. No. 2,150,630 discloses an ultrasonic probe for accurately measuring speeds and flow rates in piping in which corrosive liquids are circulating, in particular ergol used in liquid propellant rockets under pressures of 50 bars. The probe according to this French Patent comprises a protective sleeve and a single element which is in the form of a thick tube and closed at one end by a thin wall. The internal face of the tube is in electrical and mechanical contact with a piezoelectric plate, which is in contact with a damping cylinder. The sleeve completely protects the internal elements of the probe against the mechanical or corrosive actions of the measuring medium whilst enabling passage of the ultrasonic beams without prohibitive absorption.

A first difficulty encountered in manufacturing these probes is the machining of the thin wall whose thickness is approximately of 0.1 mm, and the parallelism of whose faces must be carried out accurately. Another difficulty is the mechanical and electrical connection of the active face of the piezoelectric plate contacting with the thin wall. In effect, piezoelectric material of the plate has been selected for such types of measurements as a result of its own properties, such as its sensitivity and its ability to support the high temperature of the probing medium.

For the accurate measurement of speeds and in particular low speeds, for example 1 cm/sec, and flow rates, a piezoelectric material having high sensitivity is selected. This condition is accomplished for the probe according to the above-mentioned French Patent. The piezoelectric plate is made of lead zirconate-titanate. The connection between the active face of the piezoelectric plate and the thin wall of the thick tube is constituted by a thin layer of solid conducting adhesive, such as an epoxy resin charged with silver powder. The connection attained in this way resists temperatures of up to 130° C.; the probe may be used to a maximum temperature of 100° C. and a pressure of approximately 100 bars.

In addition the French Pat. No. 2,063,324 discloses an ultrasonic probe for locating metallic parts immersed in a high temperature liquid metal. The ultrasonic probe comprises a transducing piezoelectric capsule made of lithium niobate and a damping cylinder which are curvated in a leak-tight metallic casing with thin front wall. The two faces of the piezoelectric capsule are coated with a thin silver coating then by a layer of copper deposited by electrolysis on the thin silver coating. The fixing of the two piezoelectric capsule faces onto the thin wall of the casing and onto the damping cylinder is carried out by silver brazing.

It is noted that a connection of this type is possible on account of the nature of the material constituting the piezoelectric capsule, i.e. the lithium niobate, whose Curie point is approximately 1200° C. However the low sensitivity of this material, which is adequate for the above purpose, that is the location of immersed objects, is not suitable for the accurate measurement of liquid speeds or flow rates.

The problem of the accurate measurement of speeds or flow rates of liquids under pressure and at high temperatures by means of ultrasonic probes has therefore not been satisfactorily solved as the sensitive piezoelectric materials have a relatively low Curie point which prevents the use of brazing techniques, whereas piezoelectric materials having a high Curie point do not have adequate sensitivity.

OBJECTS OF THE INVENTION

The main object of the present invention is to provide a simple and inexpensive constructional solution for the connection of the active face of the transducing piezoelectric element and the thin wall of the probe.

Another object of the invention is to provide an ultrasonic probe which has not the constructional difficulties and the temperature limits for known probes.

A further object of this invention is to provide an ultrasonic probe having a high sensitivity for accurate measurement of speeds and flow rates of liquids. It is a still another object of this invention to provide a leak-tight piezoelectric probe.

SUMMARY OF THE INVENTION

The ultrasonic probe according to the invention comprises a leak-tight protective sleeve which is generally in the form of a tube and has an end face closed by a thin metallic wall. The protective sleeve contained internal elements which are in particular a transducing piezoelectric plate and a damping cylinder. The piezoelectric element has one face which is in mechanical and electrical contact with the internal face of the thin sleeve wall and the other face which is supported on a damping cylinder. The main feature of the ultrasonic probe is that the thin sleeve wall of the sleeve end face is constituted by a metallic layer obtained by cathodic sputtering.

It can be seen that the application of a technique for metallic depositing by cathodic sputtering to the composition of the thin sleeve wall ensures a close contact with the material of the piezoelectric element or with a metallic layer with which the piezoelectric plate may be coated, without changing the properties of the ultrasonic probe since the temperature increase is negligeable, and enables a leak-tight wall of predetermined thickness to be conveniently constructed.

An additional arrangement according to the invention consists in that assembly of the internal elements of the ultrasonic probe which are included in the protective sleeve, is carried out in such a way that they are fixed by bending of the protective sleeve before the cathodic sputtering.

BRIEF DESCRIPTION OF THE DRAWINGS

The advantageous of the present invention will be apparent from the following more particular description of preferred embodiments of the invention with reference to the accompanying drawings in which.

DESCRIPTION OF THE PREFERRED EMBODIMENTS

Figure 1:
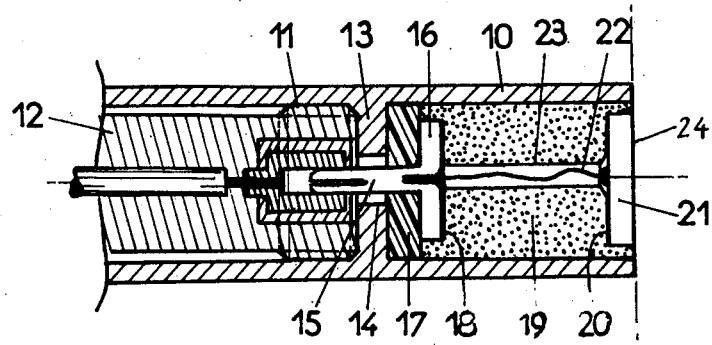
FIG. 1 is a schematic section of a probe according to the invention.

In FIG. 1, the ultrasonic probe comprises a thick protective sleeve 10, which is made of stainless steel and is of a generally cylindrical form. The hollow rear part of the sleeve 10 is provided with an internal threading 11 in which the threaded end of a support 12 is screwed. A transverse partition 13 of the sleeve 10 divides the rear part and the front part of the sleeve and is provided with an axial passage 14 through which passes an electrical contact plug 15. The base plate 16 of the plug 15 is insulated from the sleeve 10 by an insulating washer 17 and is glued by means of a ceramic or epoxy adhesive in a rear recess 18 of a damping cylinder 19 made of boron nitride. The opposite front end of the cylinder has a front recess 20 in which is disposed a transducing piezoelectric plate 21. The plate 21 is made of lead zirconate-titanate and has a thickness of 0.5 millimeters. The piezoelectric plate 21 is provided with both faces of a metal layer such as silver layer which constitute the electrodes of the plate 21 in a known way. A conductor 22 passes through an axial passage 23 of the damping cylinder 19. One of ends of the conductor 22 is brazed onto the internal rear face of the plate 21 and other end of the conductor 22 is connected to the contact plug 15.

The internal face of the pizeoelectric plate 21 is glued by means of a ceramic or epoxy adhesive in the front recess 20 of the damping cylinder 19.

As the ultrasonic probe is designed to operate at a temperature of 200° C., it is important to eliminate the possible play of the internal elements 15, 19 and 21 on account of dilation of the sleeve 10. For this purpose, the internal elements which are contained in the probe, such as the piezoelectric plate 21, the damping cylinder 19 and the contact plug 15, are inserted and fixed in position at room temperature by binding operation into the body of the sleeve 10 which has been previously heated to a temperature at least equal to the operating of the ultrasonic probe, for example to a temperature of 220° C.

Subsequently rectification of the surfaces abutting onto the front end face 24 of the probe is carried out in order to provide a plane perpendicular to the longitudinal axis of the probe.

Figure 2:
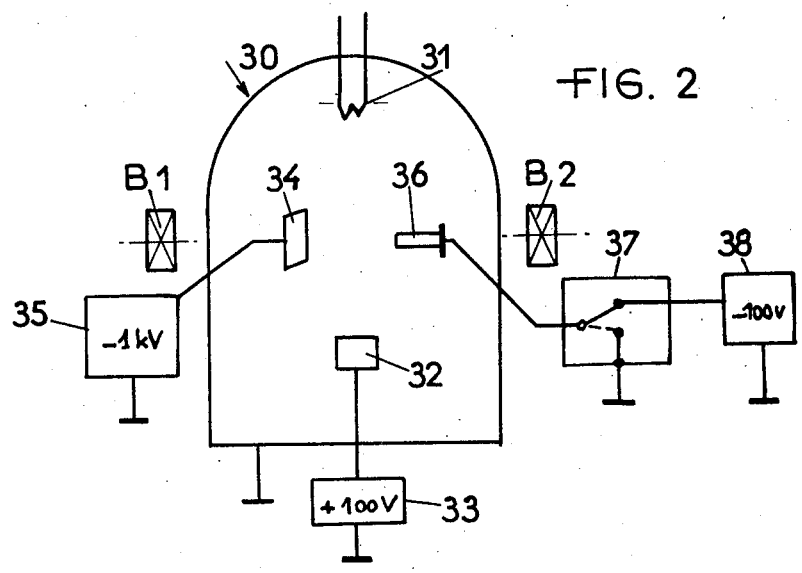
FIG. 2 is a diagram of a plant for constructing the thin wall of the probe.

To construct the thin end wall of the sleeve 10, which is included between the front face of the piezoelectric plate 21 and the front face 24 of the probe, the probe, prepared as above, is arranged, as shown in FIG. 2, in a metal coated vacuum housing 30 for cathodic sputtering which is filled with a gas such as argon at a pressure of 133 millipascals.

The housing 30 comprises a thermionic cathode 31 which includes a tungsten filament heated to 2500° C., and an anode 32 which is connected to a voltage source 33. The electrons produced by the cathode 31 are accelerated in the electrical field produced by the anode 32 at a continuous voltage of +100 V with respect to the cathode 31. Coils such as B1 and B2 produce an electrical field which concentrates the plasma, extends the electron path and increases the possibility of ionisation of the electrons as a result of collision with the gas molecules. A cathode 34 is connected to a high voltage source 35 and is raised to a negative voltage of 1 kV. An anode 36 which constitutes the ultrasonic probe, is disposed opposite the cathode 34 and is connected by means of a switch 37 to earth, except during an ionic cleaning stage preceding the deposit for which the anode 36 is connected to a voltage source 38 lowering it to −100 V. The bombardment of the front face 24 of the probe 36 by the argon ions ensures that the surfaces are clean and the micro-corrugations are formed, these assisting adhesion of the subsequent metallic deposit.

The cathodic sputtering which may be attained by other methods known to those skilled in the art, is attained preferably by means of the described housing, called triode assembly, and which has the advantage of separating the phenomena of ion production (anode-cathode assembly 31, 32) and ejection of material from the cathode 34. A further advantage is that the polarisation voltages and the gas pressure required are relatively low. In addition, as the substrate to be metal coated, i.e. the front face 24 of the ultrasonic probe, is outside the produced plasma, deterioration of the properties of the piezoelectric material are eliminated since there is no particular heating of the surface of the front face of the piezoelectric plate 21 on which the metallic deposit is carried out.

With the housing described above, a thin wall having a diameter of 10 millimeters and a thickness of 140 microns is achieved, this wall being composed of a copper and nickel based alloy, by cathodic sputtering in approximately 10 hours.

Metallographic tests and tests in working conditions have demonstrated the absolute reliability of the thin wall constructed in this way.

Ultrasonic probes constructed in accordance with the invention support temperature cycles of 200° C. and a pressure of 200 bars without noticeable deterioration of their efficiency.

By way of example, the probes according to the invention enable measurements of flow in working temperature and pressure conditions to be carried out with an absolute error of $5.10^{-3}$ for liquid flow speeds between 0.1 and 10 m/sec.

The invention also relates to the construction of probes having a damping cylinder which conducts electricity.

Figure 3:
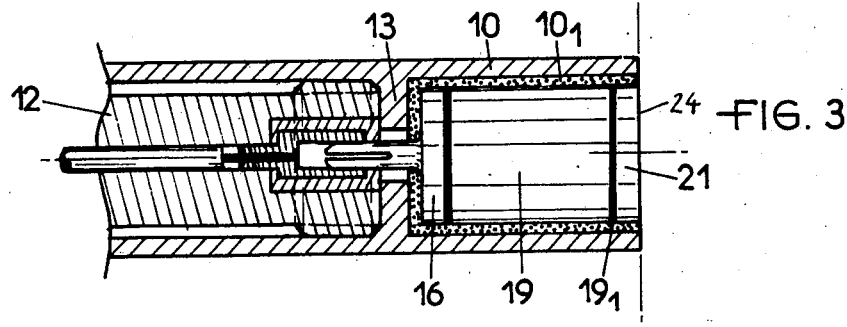
FIG. 3 is a schematic section of a probe according to the invention, in another embodiment.

The ultrasonic probe shown in FIG. 3, in which the elements identical to those of FIG. 1 are numbered the same, comprises an insulating ring $10_1$ in boron nitride which is inserted into the sleeve 10. The bottom base of the ring $10_1$ is supported on the front face of the partition 13 of the sleeve 10. In the ring $10_1$ are inserted the base plate 16 of the contact plug 15, the damping cylinder 19 and the piezoelectric plate 21.

The piezoelectric plate 21 made of ceramics with lead zirconate-titanate is fixed to the lead cylinder 19 by means of a layer of conducting adhesive $19_1$ which is constituted for example by an epoxy resin charged with silver powder. The same resin is used to fix the base plate 16 of the contact plug 15 to the damping cylinder 19.

The internal elements such as 15, 19 and 21 of the probe are inserted at room temperature into the body of the sleeve 10 which has previously been heated to a temperature which is sufficient to ensure that they are maintained by binding operation whilst operating at high temperature.

The surfaces abutting onto the front end face 24 of the probe are then rectified, and then metal is deposited by cathodic sputtering as in the example of FIG. 1.

As the invention enables close contact of the thin wall of a probe with the active face of the piezoelectric plate without requiring the interposition of seals (adhesive or brazing), it provides an advantageous method of manufacturing ultrasonic probes.

The technique used for the construction of the thin wall is particularly suited to industrial manufacturing methods in which the walls of about one hundred probes may be produced simultaneously in the same housing.

Finally, it will be noted that the ultrasonic probe according to the invention is also designed for cryogenic measurements, such as in liquid nitrogen or liquid oxygen at temperature of approximately −250° C. and under pressure of approximately 100 to 150 bars. In this case the ultrasonic probe is inserted in test piping for fee turbopumps of engine motors.

What we claim is:

1. An ultrasonic probe for measuring liquids at high temperature and under high pressure, comprising a leak-tight protective sleeve having an end face closed by a thin metallic wall and a transducing piezoelectric element having one of its two faces in mechanical and electrical contact with said thin wall, said thin sleeve wall of said sleeve end face being constituted by a metal layer obtained by cathodic sputtering.

2. An ultrasonic probe according to claim 1, in which said metal layer is deposited by said cathodic sputtering on a metal layer previously deposited on at least said piezoelectric element face.

3. An ultrasonic probe according to claim 1, in which said metal layer is deposited by said cathodic sputtering directly on the material constituting said piezoelectric element face, to be in contact with said thin sleeve wall.

4. An ultrasonic probe for measuring liquids at high temperature and under high pressure, comprising a leak-tight protective sleeve having an end face closed by a thin metallic wall and internal elements contained in said sleeve and including at least a transducing piezoelectric element having one of its faces in mechanical and electrical contact with said their sleeve wall which is constituted by a metal layer obtained by cathodic sputtering, said internal elements being fixed in position by binding of said protective sleeve before said cathodic sputtering.

5. An ultrasonic probe according to claim 4, in which said internal elements are inserted at room temperature into the said protective sleeve which has previously been raised to a temperature at least equal to operating temperature of said ultrasonic probe.

* * * * *